United States Patent [19]

Hancock et al.

[11] 4,257,916
[45] Mar. 24, 1981

[54] PROCESS FOR THE PREPARATION OF A FUNCTIONALIZED SOLID PRODUCT

[75] Inventors: Ronald D. Hancock, Weybridge; Jennie M. Kirk, Ashford, both of England

[73] Assignee: The British Petroleum Company Limited, London, England

[21] Appl. No.: 68,143

[22] Filed: Aug. 20, 1979

[30] Foreign Application Priority Data

Sep. 5, 1978 [GB] United Kingdom ............... 35566/78

[51] Int. Cl.$^3$ .................... B01J 20/32; B01J 31/02; B01J 31/12; B05D 7/00
[52] U.S. Cl. .................... 252/430; 252/428; 252/431 R; 427/219
[58] Field of Search ........... 252/430, 428, 426, 431 R; 260/513 B; 210/31 C; 521/33; 526/344; 427/219

[56] References Cited

U.S. PATENT DOCUMENTS

| 3,956,179 | 5/1976 | Sebastian et al. | 252/430 |
| 4,034,139 | 7/1977 | Mazarguil et al. | 252/430 |

FOREIGN PATENT DOCUMENTS

| 760379 | 10/1956 | United Kingdom | 260/513 B |
| 1460315 | 1/1977 | United Kingdom . | |
| 1506226 | 4/1978 | United Kingdom . | |

Primary Examiner—P. E. Konopka
Attorney, Agent, or Firm—Morgan, Finnegan, Pine, Foley & Lee

[57] ABSTRACT

A functionalized solid product containing sulphonate or sulphonic acid groups is prepared from an inorganic oxide containing surface hydroxy groups, e.g. silica by reacting the latter in a first stage with a haloalkyl alkoxy- or aryloxysilane. The first stage product is then reacted with an aqueous solution of an inorganic sulphite to give a product containing sulphonate groups. These can be converted to sulphonic acid groups by an optional third stage treatment with dilute mineral acid. The final products are suitable for use as adsorbent materials or catalyst supports.

10 Claims, No Drawings

PROCESS FOR THE PREPARATION OF A FUNCTIONALIZED SOLID PRODUCT

This invention relates to a process for the preparation of a product suitable for use as an adsorbent material or as a catalyst support.

British patent specification No. 1460315 discloses a process for the chemical modification of the surface of an inorganic substance containing hydroxyl groups, which comprises:

(a) treating the surface of said substance with an alkyl halosilane containing at least one alkyl group having 1-18 carbon atoms, said alkyl group optionally having a reactive halogen substituent, so that the alkyl halosilane reacts with hydroxyl groups on said surface to form —O—Si—R groups attached by the depicted oxygen atom to said surface, R being an alkyl group optionally having a reactive halogen substituent;

(b) where R does not have a reactive halogen substituent, introducing by halogenation or sulphochlorination a reactive halogen or sulphochloride substituent into the R group; and (c) reacting said reactive halogen or sulphochloride substituent with a suitable compound to introduce into the alkyl group one or more of the following groups: sulphonic acid, amino, substituted amino, trialkyl ammonium, thiol, ether, thioether, hydroxyl, nitrile, nitro, carboxyl and hydrazine.

Because alkyl halosilanes are susceptible to hydrolysis, considerable care must be taken in their use, for example, atmospheric moisture must be rigorously excluded. Furthermore, during the reaction of the alkyl halosilane with the inorganic substance containing hydroxyl groups, hydrogen halide is produced. This is an undesirable by-product which may result in degradation of the functionalised product.

British patent specification No. 1506226 discloses a method of chemically modifying the surface of an inorganic solid having reactive hydroxyl groups thereon, which comprises reacting, under dry conditions and in the presence of a primary amine or organic sulphonic acid catalyst, the surface of the said solid with an alkyl, aryl or aralkyl-substituted alkoxysilane, at least one of the said alkyl, aryl or aralkyl substituents containing one or more functional groups which are:

—SO₃H, —SH, —OH, —CN,
—NO₂, —COOH,

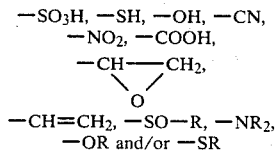

—CH=CH₂, —SO—R, —NR₂,
—OR and/or —SR wherein R is an alkyl group, whereby the said reactive hydroxyl groups react with the alkoxy groups of the said silane.

1506226 further discloses that alkoxysilanes are normally slow reacting substances and that the reaction rate is accelerated by use of a catalyst. It also states the necessity for dry conditions.

We have now discovered a process for the preparation of a functionalised solid product which does not require stringent precautions to exclude moisture nor does it require the use of a catalyst.

Thus according to the present invention there is provided a process for the preparation of a product, derived from an inorganic oxide containing surface hydroxyl groups, containing groups of general formula (I) and/or (II).

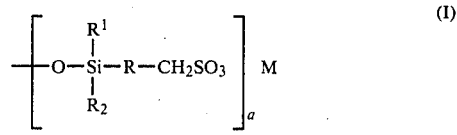

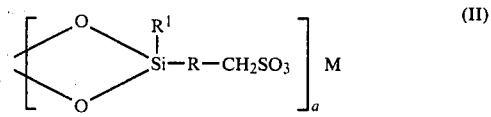

wherein R is a divalent radical containing up to 20 carbon atoms, R¹ and R² are alkoxy or aryloxy groups containing up to 20 carbon atoms, or hydrolysis products thereof, M is metallic or hydrogen ion and (a) is an integer corresponding to the valency of M, which process comprises reacting an inorganic oxide containing surface hydroxyl groups in a first stage with a compound of formula (III)

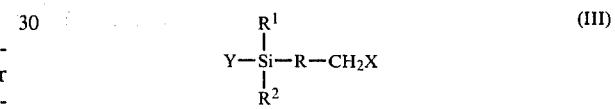

wherein R, R¹ and R² are as hereinbefore defined, Y is a halogen atom or an alkoxy or aryloxy group containing up to 20 carbon atoms and X is a halogen atom; and reacting the product of the first stage in a second stage with an aqueous solution of a water soluble inorganic sulphite to form a sulphonate salt; and optionally reacting the sulphonate salt of the second stage with dilute mineral acid in a third stage to form a product containing sulphonic acid groups.

Suitable inorganic oxides containing surface hydroxyl groups include alumina, titania, zirconia, glass, sepiolite and zeolite molecular sieves. Preferably the inorganic oxide is silica and more preferably silica gel. In addition, mixtures of inorganic solids may be used. Unless they have been subjected to severe treatment, e.g. heating above 1000° C., commercial silicas contain surface hydroxyl groups.

Preferably the groups R¹, R² and Y are alkoxy groups containing 1-3 carbon atoms or hydrolysis products thereof. Most preferably they are identical groups.

R is preferably an alkylene group containing up to 6 carbon atoms, most preferably a di- or tri-methylene group.

Preferred haloalkyl alkoxysilanes include γ-chloro- and γ-bromotrimethoxysilane.

In the case of silica and the compound of formula (III) the first stage product is believed to be formed by the reaction represented by the following equation or a similar reaction involving condensation with both Y and R²:

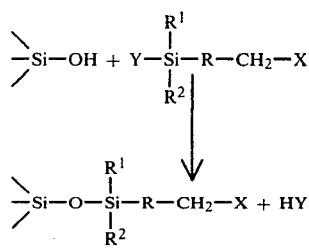

However the invention is not intended to be restricted in any way by the above equation representing the formation of the substrate.

In the first stage the reaction may be effected at room temperature or by warming the reactants together or under reflux in the presence or absence of an inert solvent for the compound of formula (III) and thereafter isolating the product. The preferred solvent for the compound of formula (III) is toluene. Other suitable solvents include benzene, heptane, dichloromethane, acetone and tetrahydrofuran.

In the second stage the reaction between the first stage product and the sulphite may also take place at room temperature or preferably with the application of heat.

The reaction is believed to be represented by the following equation, again taking silica as typical of the inorganic solid, and sodium sulphite to be typical of the sulphite:

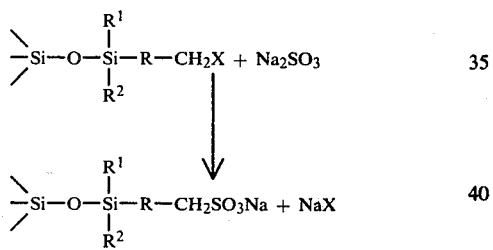

In the optional third stage, the sulphonate groups of the second stage are reacted with dilute mineral acid, preferably dilute nitric acid, at ambient temperature to convert them to sulphonic acid groups.

The invention is illustrated with reference to the following Examples.

EXAMPLE 1

Silica gel (50 g) was suspended in toluene (250 ml) and the reaction mixture stirred at reflux temperature for 30 minutes during which time any water liberated was collected in a Dean and Stark receiver. After cooling, water (5 ml) was added and the reactor contents stirred for 2 hours. The silane $(MeO)_3SiCH_2CH_2CH_2Cl$ (40 ml) was then added and the mixture stirred at reflux temperature for 4 hours. The silica product was isolated, Soxhlet extracted with methanol for 15 hours and then dried in vacuo. To this chloro-silica was added a saturated aqueous solution of sodium sulphite (200 ml) and the mixture stirred at reflux temperature for 18 hours to form a sulphonate. After cooling, the silica was isolated by filtration, washed free from residual sodium sulphite with water, acidified with 0.5 N nitric acid (500 ml) to form the sulphonic acid derivative, washed free from residual nitric acid with water and finally dried in vacuo. On analysis the silica was found to contain 0.45 percent weight sulphur.

EXAMPLE 2

Silica gel (90 g) was suspended in toluene (250 ml) and γ-chloropropyltrimethoxysilane (45 ml) added. The reaction mixture was then stirred under nitrogen at reflux temperature for four hours. The silica product was isolated, Soxhlet extracted with methanol for 18 hours and vacuum dried. To this chloro-silica was added a saturated aqueous solution of sodium sulphite (250 ml) and the mixture was stirred and refluxed under nitrogen for 18 hours. After cooling the silica product was isolated and washed with distilled water to remove any residual sulphite. The silica was then acidified with 1 N nitric acid and finally washed with distilled water and vacuum dried. On analysis the silica was found to contain 0.6 percent weight sulphur.

EXAMPLE 3

Silica gel (80 g) was suspended in toluene (200 ml) and γ-chloropropyltrimethoxysilane (40 ml) was added. The reaction mixture was then stirred and refluxed under nitrogen for four hours. The silica was then isolated, Soxhlet extracted with methanol for 16 hours and vacuum dried. This product was then stirred and refluxed under nitrogen in a saturated aqueous solution of sodium sulphite. After cooling, the product was isolated, washed with distilled water and vacuum dried. On analysis the silica was found to contain 1.6 percent sulphur and 1.6 percent sodium.

We claim:

1. A process for the production of a product containing groups of general formula (I)

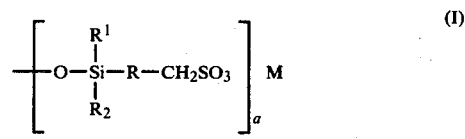

wherein R is a divalent radical containing up to 20 carbon atoms, $R^1$ and $R^2$ are alkoxy or aryloxy groups containing up to 20 carbon atoms, or hydrolysis products thereof, M is a metallic ion and (a) is an integer corresponding to the valency of M, which process comprises reacting an inorganic oxide containing surface hydroxyl groups selected from the group consisting of alumina, titania, zirconia, glass, sepiolite, a zeolite molecular sieve and silica in a first stage with a compound of general formula (III)

wherein R, $R^1$ and $R^2$ are as hereinbefore defined, Y is a halogen atom or an alkoxy or aryloxy group containing up to 20 carbon atoms and X is a chlorine atom, characterized by the fact that the reaction is effected in the absence of a catalyst and the reaction product of the first stage is reacted in a second stage with an aqueous solution of a water soluble inorganic sulphite to form a sulphonate salt.

2. A process for the production of a product containing groups of general formula (II)

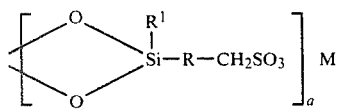

wherein R is a divalent radical containing up to 20 carbon atoms, $R^1$ is an alkoxy or aryloxy groups containing up to 20 carbon atoms, or hydrolysis products thereof, M is a metallic ion and (a) is an integer corresponding to the valency of M, which process comprises reacting an inorganic oxide containing surface hydroxyl groups selected from the group consisting of alumina, titania, zirconia, glass, sepiolite, a zeolite molecular sieve and silica, in a first stage with a compound of general formula (III)

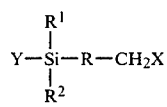

wherein R and $R^1$ are as hereinbefore defined and $R^2$ is an alkoxy or aryloxy group or hydrolysis product thereof, Y is a halogen atom or an alkoxy or aryloxy group containing up to 20 carbon atoms and X is a chlorine atom, characterised by the fact that the reaction is effected in the absence of a catalyst and the reaction product of the first stage is reacted in a second stage with an aqueous solution of a water soluble inorganic sulphite to form a sulphonate salt.

3. A process according to claim 1 characterized by the fact that sulphonate salt of the second stage is reacted with dilute mineral acid to form a product containing sulphonic acid groups and having the general formula I except that M is hydrogen.

4. A process according to claim 2 characterized by the fact that sulphonate salt of the second stage is reacted with dilute mineral acid to form a product containing sulphonic acid groups and having the general formula II except that M is hydrogen.

5. A process according to claims 1 or 2 characterized by the fact that the compound of general formula (III) is gamma-chloropropyl trimethoxysilane.

6. A process according to claims 1 or 2 characterized by the fact that the water soluble inorganic sulphite is sodium sulphite.

7. A process according to claims 1 or 2 characterized by the fact that the first stage is carried out at a temperature in the range room temperature to 300° C. in the presence of a solvent.

8. A process according to claims 1 or 2 characterized by the fact that the solvent is toluene.

9. A process according to claims 1 or 2 wherein the second stage is carried out at a temperature in the range room temperature to the reflux temperature of the aqueous solution.

10. A process according to claims 1 or 2 characterized by the fact that the dilute material acid is nitric acid.

* * * * *